(12) United States Patent
Wiessler et al.

(10) Patent No.: US 6,211,356 B1
(45) Date of Patent: Apr. 3, 2001

(54) METALLOCENE-PHOSPHORAMIDITE CONJUGATES, PROCESS FOR THEIR PREPARATION AND THEIR USE

(75) Inventors: Manfred Wiessler, Heidelberg; Dagmar Schütte, Dossenheim, both of (DE)

(73) Assignee: Deutsches Krebsforschungszentrum Stiftung des Offentlichen Rechts, Heidelberg (DE)

(*) Notice: Subject to any disclaimer, the term of this patent is extended or adjusted under 35 U.S.C. 154(b) by 0 days.

(21) Appl. No.: 09/029,954

(22) PCT Filed: Sep. 6, 1996

(86) PCT No.: PCT/DE96/01681

§ 371 Date: Oct. 21, 1998

§ 102(e) Date: Oct. 21, 1998

(87) PCT Pub. No.: WO97/09337

PCT Pub. Date: Mar. 13, 1997

(30) Foreign Application Priority Data

Sep. 7, 1995 (DE) .............................. 195 33 093

(51) Int. Cl.[7] .......................... C07H 23/00; C07H 19/04; C07F 17/02; A61K 31/70
(52) U.S. Cl. ..................... 536/26.6; 536/26.1; 536/121; 514/44; 514/52; 556/143
(58) Field of Search ...................... 514/44, 52; 536/17.1, 536/26.1, 26.6, 121; 556/143

(56) References Cited

PUBLICATIONS

Nucleic Acids in Chemistry and Biology, edited by Blackburn and Gait, published by IRL Press, pp. 114–115, 1992.*
"Glossary of Class Names of Organic Compounds", IUPAC—Pure and Applied Chemistry, vol. 67, p. 1358, 1995.*

Khan et al., "Automated solid–phase synthesis of metallo–oligonucleotides.", Book of Abstracts, 216th ACS National Meeting, Boston, MA Aug. 23–27, 1998, publisher: ACS, Washington D.C., p.: INOR–653.*

Kenten et al., "Improved Electrochemiluminescent Label for DNA Probe Assays: Rapid Quantitative Assays of HIV–1 Polymerase Chain Reaction Products", Clin. Chem., vol. 38(6): 873–879, (1992).*

Bannwarth et al., "A Simple Specific Labelling For Oligonucleotides by Bathophenanthroline–Ru(III) Complexes as Nonradioactive Label Molecules", Tetrahedron Letters, vol. 30(12): 1513–1516, (1989).*

Advanced Inorganic Chemistry (Fifth Edition), edited by Cotton and Wilkinson, John Wiley & Sons, pp. 77–83 and 878–879, (1988).*

Mucic et al., 1996, "Synthesis and Characterization of DNA with Ferrocenyl Groups Attached to Their 5'–Termini: Electrochemical Characterization of a Redox–Active Nucleotide Monolayer," *Chemical Communications* 4:555–557.

Debitsudo, A., 1994, "Preparation of Oligonucleotide having Redox Group," *Chem. Abstr.* 121(11):Abstract No. 134702f.

* cited by examiner

Primary Examiner—Howard C. Lee
(74) Attorney, Agent, or Firm—Pennie & Edmonds LLP

(57) ABSTRACT

The invention concerns metallocene-phosphoramidite conjugates comprising one or a plurality of metallocenes and one or a plurality of phosphoramidites. The invention further concerns a process for preparing the metallocene-phosphoramidite conjugates and their use.

14 Claims, 2 Drawing Sheets

METALLOCENE-PHOSPHORAMIDITE CONJUGATES, PROCESS FOR THEIR PREPARATION AND THEIR USE

This is a national phase filing of the Application No. PCT/DE96/01681, which was filed with the Patent Corporation Treaty on Sep. 6, 1996, and is entitled to priority of the German Patent Application P 195 33 093.5, filed Sep. 7, 1995.

FIELD OF THE INVENTION

The present invention relates to metallocene-phosphoramidite conjugates, a process for their preparation as well as their use.

BACKGROUND OF THE INVENTION

The detection and/or differentiation of oligonucleotides and portions of DNA and RNA, respectively, with an electron microscope has caused difficulties so far. Up to the present, there is no satisfactory possibility of visualizing DNA and RNA by electron microscopy in a reproducible manner to carry out studies therewith.

Therefore, it is the object of the present invention to provide a product by which a signal can be attached to the DNA and/or RNA already during the synthesis, if possible, by simply modifying the DNA and/or RNA so as to render the DNA and/or RNA better detectable by means of an electron microscope.

This object is achieved by the features of claims 1, 9, 12 and 14. Advantageous embodiments follow from the dependent claims.

SUMMARY OF THE INVENTION

The invention concerns metallocene-phosphoramidite conjugates comprising one or a plurality of metallocenes and one or a plurality of phosphoramidites. The invention further concerns a process for preparing the metallocene-phosphoramidite conjugates and their use.

DETAILED DESCRIPTION OF THE INVENTION

It is the object of the present invention to provide a product by which a signal can be attached to the DNA and/or RNA already during the synthesis, if possible, by simply modifying the DNA and/or RNA so as to render the DNA and/or RNA better detectable by means of an electron microscope.

The metallocene-phosphoramidite conjugate according to the invention relates to conjugates of one or a plurality of phosphoramidites to one or a plurality of metallocenes, preferably transitional metal metallocenes, particularly ferrocene, ruthenocene or osmocene. In this connection, the metallocenes occurring in a conjugate may be equal or different. Preferably, there is also a spacer, e.g., a $C_1$ to $C_{10}$ alkyl spacer, preferentially a propyl or butyl group, between phosphoramidite and metallocene.

The metallocene-phosphoramidite conjugate according to the invention is preferably a metallocenylalkyl-(2-cyanoethyl)-diisopropylamidophosphite, the metal being a transitional metal, preferentially Fe, Ru or Os.

The metallocene-phosphoramidite conjugate according to the invention is preferably added to a solid phase-coupled oligomer in the course of the oligonucleotide synthesis. Good results are achieved when the metallocene-phosphoramidite conjugate is used in excess as compared to the oligonucleotides. Metallocene labeling of the DNA or RNA then occurs during the oligonucleotide synthesis, which—as a result thereof—becomes well investigatable by means of an electron microscope. Of course, it is also possible to subsequently label the DNA and RNA with the metallocene by means of the conjugate. Fine structures of DNA and/or RNA can be investigated with an electron microscope by the metallocene-labeled oligonucleotides. Antisense oligonucleotides can be investigated as to their hybridization properties, a distinction can be made between specific and non-specific linkages, and the double or triple helix formation can be observed. When the sequence is known, the structures can be attributed to the sequence with an electron microscope. Moreover, a preferred hybridization can be measured when various oligonucleotides are labeled with differing metallocenes. In this connection, individual metal atoms can be detected by means of electron loss spectroscopy on the basis of their characteristic electron spectra.

Figure 1:
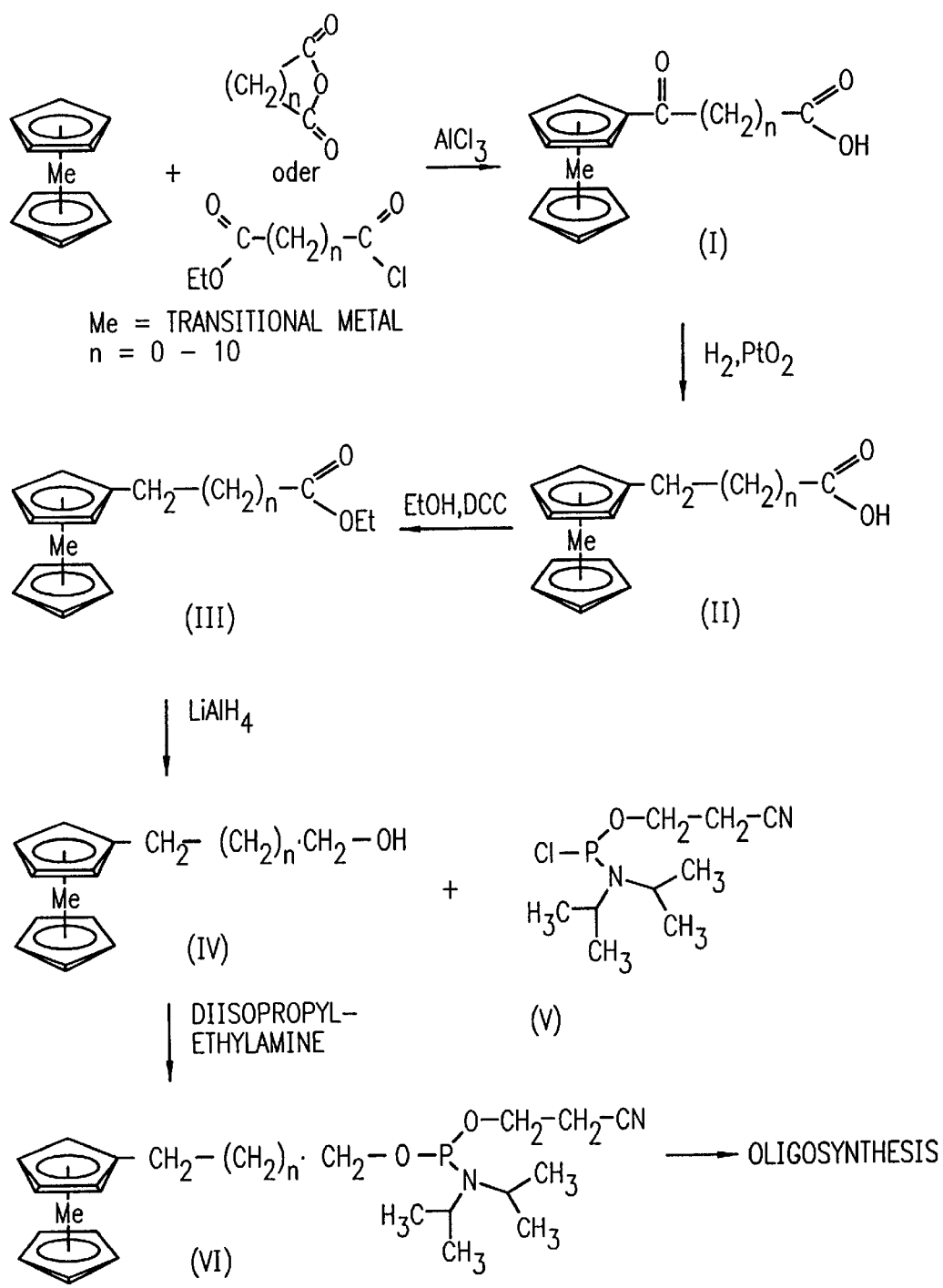
FIG. 1 depicts an exemplary reaction scheme for the preparation of a metallocene-phosphoramidite conjugate.

The metallocene-phosphoramidite conjugates are prepared, e.g., by means of a process whose reaction scheme is shown in FIG. 1: A metallocene (transitional metal, preferably ferrocene, ruthenocene or osmocene) is reacted with a dicarboxylic acid chloride or anhydride by catalysis of a Friedel-Crafts catalyst to give metallocenoylalkyl carboxylic acid (I). The keto function in the molecule is then hydrogenated under suitable conditions, e.g., hydrogenation by catalysis of a $PtO_2$ catalyst (II). The carboxylic acid function in the molecule is then esterified by reaction with an alcohol (III) and thereafter reduced under suitable conditions, e.g., by reaction with $LiAlH_4$ (IV). The resulting alcohol (IV) can be reacted with a phosphoramidite derivative, e.g., chloro-N,N-diisopropylamino-cyanoethoxyphosphite (V) common in the oligonucleotide synthesis. The resulting conjugate comprising metallocene and phosphoramidite (VI) can now be used in the oligonucleotide synthesis.

Figure 2:
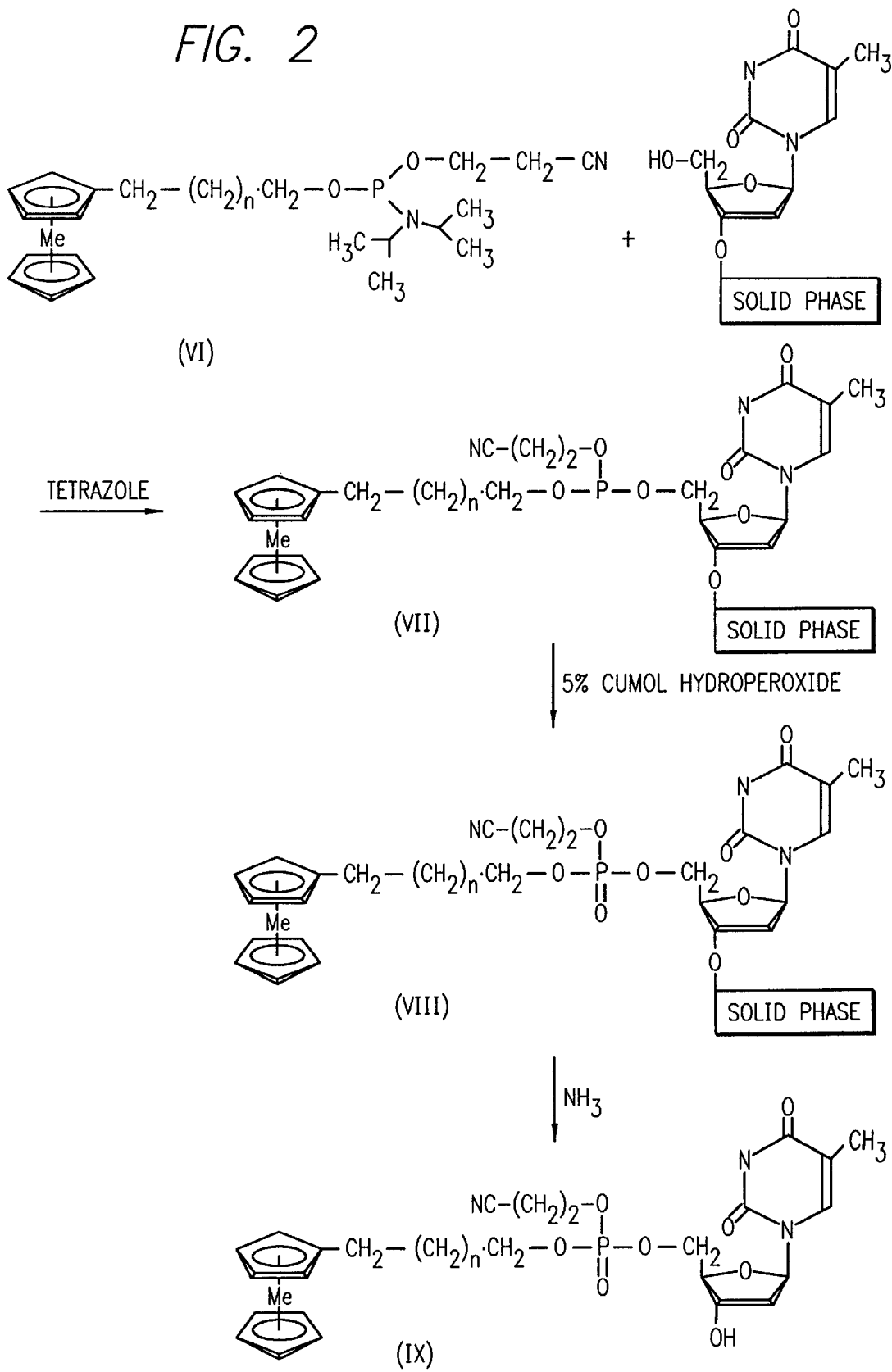
FIG. 2 depicts the use of the metallocene-phosphoramidite conjugate in the oligosynthesis for labeling oligonucleotides with metallocenes.

The labeling of (oligo)nucleotides during the synthesis thereof is shown in FIG. 2. The reaction scheme shown in FIG. 2 is representative of the linkage of the (oligo)nucleotide to the metallocene, which takes place by reacting metallocene-phosphoramidite conjugate with a nucleotide or oligonucleotide. Thus, the metallocene-phosphoramidite conjugate according to the invention (VI) is reacted with a solid phase-linked 5'-OH-free (oligo)nucleotide by means of an activator, e.g., tetrazole. The resulting compound (VII) is reacted with an oxidant, e.g., dilute peroxide solution, particularly 5% cumene hydroperoxide solution, with a compound (VIII) forming. The nucleotide linked to the metallocene is separated from the solid phase upon exposure to a base, e.g., ammonia, with the compound (IX) forming.

The inventors have found that in addition to the good analyzability with an electron microscope the (oligo)nucleotides labeled by the metallocenes can be applied in interesting manner, namely as artificial restriction enzymes. It is generally known that foreign substances can be converted in the body into a water-soluble form by oxidation. The hydrogen peroxide required for this purpose is made of oxygen initially by reducing it to give a superoxide anion ($O_2^-$). This anion can disproportionate with the aid of superoxide dismutase to give oxygen and hydrogen peroxide. If iron (II) ions are present, the intermediarily forming $H_2O_2$ can be reacted to give hydroxyl radicals which represent a highly reactive species. If this reaction takes place in the vicinity of DNA, the DNA can be cleaved in a way similar to that effected by a restriction enzyme. If the cleavage is induced artificially, a reducing agent will be added, e.g., dithiotreitol (DTT), which again converts iron (III) into iron(II) which can react again. Ferrocene may trigger this reaction as iron(II)-containing substance. If a ferrocene-labeled oligonucleotide is used, the iron(II) ion in the close vicinity of the DNA will be fixed to a certain sequence by the hybridization of the oligonucleotide with single-stranded DNA (thereby forming Watson-Crick base pairing) or also double-stranded DNA (thereby forming Hoogsteen base pairing). If the iron(II) catalyzes the cleavage of $H_2O_2$ there, a strand of the DNA breaks at a defined site because of the resulting reactive hydroxyl radicals. In the ideal case, this cutting only takes place at a specific site of the DNA. Of course, the above description also applies—in place of iron(II)—to ruthenium(II) and osmium(II) in the particular ruthenocenes and osmocenes, as well as to all transitional metal metallocenes in which the transitional metal can simply be converted into various oxidation steps by reduction and oxidation, respectively.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLES

A. Example 1

Preparation Of (5-ferrocenylpentyl)-(2-cyanoethyl)-Diisopropylamidophosphite 1. 4-Ferrocenoylbutyric Acid (I)

A mixture comprising 5.0 g (27 mmoles) of ferrocene and 2.3 g (20 mmoles) of glutaric acid anhydride in 100 ml $CH_2Cl_2$ was added dropwise to 3.5 g (26 mmoles) of aluminum trichloride in 100 ml of anhydrous $CH_2Cl_2$. In this connection, the solution turns violet. After refluxing for 3 h, the batch was hydrolyzed and sucked through a frit to remove reaction products which are not soluble in either aqueous phase or organic phase. The aqueous phase was then separated, and the organic phase was washed three times with water, dried with $NaSO_4$ and concentrated.

Yield: 3.5 g (58.3% of the theoretical) TLC: $R_f$(silica gel, $CHCl_3$/MeOH 95:5): 0.6 Column chromatography: aluminum oxide, acidic (activity III), 1) $CH_2Cl_2$; 2) $CH_2Cl_2$/MeOH 1:1+5% by vol. of HOAc $^1$H-NMR (250 MHz) $CDCl_3$; δ=4.76–4.75 (t, 2H, Cp subst.); 4.51–4.50 (t, 2H, Cp subst.); 4.19 (s, 5H, Cp unsubst.); 2.82–2.76 (t, 2H, $CH_2$—C(O)); 2.40–2.34 (t, 2H, $CH_2$—COO); 1.90–1.86 (m, 2H, C—$CH_2$—C)

Mass spectrum (MS): ($C_{15}H_{16}FeO_3$, 300.04), m/z=300 ($M^+$, 100%)

2. 5-Ferrocenylpentanoic Acid (II)

2.0 g (6.66 mmoles) of 4-ferrocenoylbutyric acid (I) were dissolved with 50 ml of glacial acetic acid in a three-neck flask, which was subsequently rinsed with nitrogen. 100 mg of platinum oxide were added as catalyst. The flask was rinsed once again with nitrogen and then charged with hydrogen. The hydrogenation is concluded after 18 h, and the catalyst is sucked off. The reaction batch is diluted with 100 ml of $H_2O$ and extracted 5 times with $CH_2Cl_2$. The combined organic phases were washed with $H_2O$ two more times, dried with $NaSO_4$, concentrated and chromatographed.

Yield: 1.91 g (98% of the theoretical) TLC: $R_f$ (silica gel, $CHCl_3$/MeOH 95:5) 0.65 Column chromatography: aluminum oxide, acidic (act. III), 1) $CH_2Cl_2$; 2) $CH_2Cl_2$/MeOH 95:5+5% by vol. of HOAc $^1$H-NMR (250 MHz) $CDCl_3$; δ=4.08 (s, 5H, Cp unsubst.); 4.03 (s, 4H, Cp subst.); 2.37–2.32 (m, 4H, Fc—$CH_2$, $CH_2$—COOH); 1.67–1.55 (m, 4H, 2×$CH_2$ [2 times $CH_2$])

Mass spectrum (MS): ($C_{15}H_{18}FeO_2$, 286.07), m/z=286 ($M^+$, 100%); 199 (Fc—$CH_2$, 31%); 121 (FeCp, 40%)

3. 5-Ferrocenylpentanoic Acid Ethyl Ester (III)

1 g (4.8 mmoles) of dicyclohexylcarbodiimide were added to 1 g (3.5 mmoles) of 5-ferrocenylpentanoic acid (II) and 500 μl of ethanol in THF and stirred overnight at room temperature. On the next day, the precipitated dicyclohexyl urea was sucked off, the reaction batch was concentrated and chromatographed without further processing.

Yield: 692 mg (63% of the theoretical) TLC: $R_f$(silica gel, $CHCl_3$); 0.8 Column chromatography: aluminum oxide, neutral (act. III), PE/EE 9:1

$^1$H-NMR (250 MHz) $CDCl_3$: δ=4.17–4.10 (q, 2H, O—$CH_2$); 4.08 (s, 5H, Cp unsubst.); 4.04–4.03 (m, 4H, Cp subst.); 2.37–2.28 (m, 4H, Fc—$CH_2$, $CH_2$—COO); 1.72–1.51 (m, 4H, 2×$CH_2$)

Mass spectrum (MS): ($C_{17}H_{22}FeO_2$, 314.09), m/z=314 ($M^+$, 32.6%); 206 ($M^+$—Cp—OEt, 49.2%); 163 (FeCp—$CH_2$—CH=$CH_2$, 83.6%), 55 ($C_4H_7$, 100%)

4. 5-Ferrocenylpentanol (IV)

61 mg (1.60 mmoles) of $LiAlH_4$ were added to 0.5 g (160 mmoles) of 5-ferrocenylpentanoic acid ethyl ester (III) in 20 ml THF and stirred at room temperature for 2 h. The batch was hydrolyzed, 50 ml of dichloromethane were added, neutralized with 2 molar hydrochloric acid and washed three times with $H_2O$, dried with $NaSO_4$ and concentrated.

Yield: 378 mg (89% of the theoretical) TLC: $R_f$ (aluminum oxide, $CH_2Cl_2$)=0.2 Column chromatography: aluminum oxide, neutr. (act. III), $CH_2Cl_2$ $^1$H-NMR (250 MHz) $CDCl_3$: δ=4.08 (s, 5H, Cp unsubst.); 4.10–4.02 (m, 4H, Cp subst.); 3.68–3.61 (dt, 2H, $CH_2$—OH); 2.37–2.31 (m, 2H, Fc—$CH_2$), 1.65–1.49 (m, 4H, 2×$CH_2$); 1.45–1.35 (m, 2H, $CH_2$)

Mass spectrum (MS): ($C_{15}H_{20}FeO$, 272.08), m/z=272 ($M^+$, 100%); 199 (Fc—$CH_2$, 20.2%)

5. (5-Ferrocenylpentyl)-(2-Cyanoethyl)-Diisopropylamido-Phosphite (VI)

0.150 g (0.55 mmole) of the 5-ferrocenylpentanol (IV) were concentrated twice with THF, taken up with 5 ml THF, and 376 μl (2.2 mmoles) of Hünig base were added. 195 μl (0.83 mmole) of chloro-N,N-diisopropylamino-cyanoethoxyphosphine (V) were added dropwise to this reaction mixture by means of a syringe via a septum. 50 μl of $H_2O$ were added at room temperature after 15 min. and stirred for another 30 minutes. The batch was taken up in 20 ml EE/$NEt_3$ and shaken out with 10% $NaHCO_3$ solution, thereafter washed 2 times with water, dried with $NaSO_4$ and concentrated.

Yield: 164 mg (94% of the theoretical) TLC: $R_f$ (aluminum oxide, $CH_2Cl_2$)=0.61 Column chromatography: silica gel, PE/EE/$NEt_3$ 18:1:1

¹H-NMR (250 MHz) CDCl₃: δ=4.08 (s, 5H, Cp unsubst.); 4.04–4.02 (m, 4H, Cp subst.); 3.89–3.75 (2 times sep., 1H each, NCHMe₂); 3.70–3.52 (m, 4H, CH₂—cyanoethyl, 5"-H₂); 2.65–2.60 (t, 2H, CH₂-CN); 2.36–2.30 (m, 2H, 1"—H₂); 1.68–1.35 (m, 6H, 3×CH₂); 1.20–1.16 (4×s, 3H each, 4×CH₃)

Mass spectrum (MS): ($C_{24}H_{37}FeN_2O_2P$, 472.19), m/z= 472 (M⁺, 14.4%); 389 (M⁺—N((CH(CH₃)₂—CN, 63.0%); 121 (FeCp, 100%)

B. Example 2

Labeling of Oligonucleotides with Ferrocene 1. (5-Ferrocenylpentyl)-2-Cyanoethyl)-(3'-O-Acetyl-2'-Deoxythymidine-5')-Phosphite Triester (VII)

50 mg (0.18 mmole) of 3'-O-acetyl-2'-deoxythymidine and 20 mg (0.29 mmole) of tetrazole were concentrated twice with 5 ml of anhydrous CH₃CN and taken up with 5 ml CH₃CN. For this purpose, 100 mg (0.21 mmole) of the phosphoramidite (VI) were slowly added dropwise to 10 ml CH₃CN which had also been concentrated twice with CH₃CN beforehand. After stirring at room temperature for 1 h, 100 ml PE/EE 9:1 were added to the batch, shaken out with 10% NaHCO₃ solution, washed two times with H₂O and concentrated.

Yield: 103 mg (88% of the theoretical) TLC: $R_f$ (silica gel, CHCl₃/MeOH 95/5)=0.5 Column chromatography: silica gel, CHCl₃/MeOH/NEt₃ 98/1/1

2. Triethylammonium-(5-Ferrocenylpentyl)-(3'-O-Acetyl-2'-Deoxythymidine-5')-Phosphate (VIII)

103 mg (0.15 mmole) of the phosphite triester (VII) were mixed with 1 ml of a 5% cumene hydroperoxide solution in CH₃CN. After 3 minutes, the reaction was stopped by the addition of 100 μl of isopropanol. The batch was mixed with 1 ml of triethylamine and carefully concentrated without further processing and immediately chromatographed. In this connection, the cyanoethoxy group is cleaved by the triethylamine.

Yield: 104 mg (93% of the theoretical) TLC: $R_f$ (silica gel, CHCl₃/MeOH 95/5)=0.2 Column chromatography: silica gel, CHCl₃/MeOH/NEt₃ 98/1/1

¹H-NMR (250 MHz) CDCl₃: δ=7.77 (q, 1H, 6-H); 6.29–6.24 (dd, 1H, 1'-H); 5.29–5.28 (dt, 1H, 3'-H); 4.12–4.08 (m, 2H, Cp subst.); 4.06 (s, 5H, Cp unsubst.); 4.05–3.98 (m, 5H, Cp subst., 4'H, 5'H₂); 3.84–3.76 (dt, 2H, 5"-H₂); 2.32–2.22 (m, 4H, 2'-H, 1"-H₂); 2.03 (s, 3H, C(O) CH₃); 1.84 (d, 3H, 5-CH₃); 1.66–1.42 (m, 6H, 3×CH₂) $J_{5-Me,6}$=1.18; $J_{1',2'}$=6.53; $J_{5',P}$=6.45, $J_{6",P}$=6.45

3. 5'-Phosphate (IX)

The phosphate diester (VIII) was mixed with 1 ml of MeOH/H₂O/NEt₃ 4:2:1. After 30 minutes, the batch was concentrated, taken up with ethanol twice and concentrated again.

¹H-NNR (250 MHz) CDCl₃: δ=7.66 (q, 1H, 6-H); 6.21–6.16 (dd, 1H, 1'-H); 4.40–4.35 (m, 1H, 3'-H); 4.22–4.20 (dd, 2H, Cp subst.); 4.10–3.87 (m, 7H, Cp subst., 4'H, 5'-H₂); 4.06 (s, 5H, Cp unsubst.); 3.81–3.73 (dt, 2H, 6"-H₂); 2.33–2.27 (m, 2H, 1"-H₂); 2.18–2.11 (m, 2H, 2'-H); 1.85 (d, 3H, 5-CH₃) 1.66–1.44 (m, 4H, 2×CH₂); 1.43–1.28 (m, 2H, CH₂) $J_{5-Me,6}$=1.22; $J_{1',2'}$=6.55; $J_{5',P}$=6.53.

C. Example 3

General Instruction as to the Synthesis of Triethylammonium-(5-Ferrocenylpentyl)-(2'-Deoxynucleoside-5')-Phosphates at the Solid Phase The columns with the solid phase usually contain 0.2 μmole of a nucleoside. However, in this case, solid phases with a 1 μmole charge were chosen to enable a spectroscopic investigation. The columns which were used in the automated oligonucleotide synthesis are made such that a Luer syringe can be mounted on both sides. In this way, the column can be rinsed with the desired reactants or solvents by forcing them from one syringe into the other. The solid phase synthesis was carried out with all of the four deoxynucleosides:

1. Cleavage of the dimethoxytrityl protective group: 2 times 1 ml of 3% dichloracetic acid in dichloromethane each for 1 minute.

2. Rinsing using the cleavage reagent until the eluate is colorless,

3. Rinsing using at least 5 times 1 ml of dichloromethane to remove any traces of acid, 4. Draining off the rest of the solvent at the water jet pump up to dryness, 5. Aeration by means of argon, 6. Linkage: 180 μl of a tetrazole solution (35 mg/ml) in acetonitrile and 23.6 mg (50 μmoles) of the phosphoramidite (VI) in 500 μl of acetonitrile are mixed and immediately placed onto the solid phase. The reaction mixture is roughly rinsed out after 3 minutes, and the procedure is repeated.

7. Rinsing using at least 5 times 1 ml of acetonitrile,

8. Oxidation: 1 ml of a 5% cumol hydroperoxide in acetonitrile for 2 minutes.

9. Rinsing using at least 5 times 1 ml of acetonitrile

10. Draining off the rest of the solvent at the water jet pump.

11. Incubation of the solid phase with 1 ml of a concentrated ammonia/methylamine solution (about 10–30% each) for 5 minutes.

12. Rinsing of the solution in an Eppendorf reaction vessel which can be screwed together and incubation at 55° C. for 1 hour.

Thereafter, the reaction batch is dissolved with 1 ml of TEAA/CH₃CN 1:1 on the lyophilizer and for further processing.

| Compound | $\lambda_{max}$Fc-dN [nm] | $\lambda_{max}$dNMP[1] [nm] | Rt time[2] [min] | OD | Yield [%] |
|---|---|---|---|---|---|
| Fc-dT | 264 | 267 | 33 | 2.28 | 23.7 |
| Fc-dC | 270 | 271 | 31 | 2.78 | 30.5 |
| Fc-dG | 252 | 252 | 24 | 3.85 | 28.8 |
| Fc-dA | 257 | 259 | 34 | 2.17 | 14.1 |

[1] according to Maniatis, Sambrook, 1989
[2] The HPLC was carried out on a preparative RP₁₈ column. Flow 4 ml/min., 25% - 75% B in 40 min. A: 90% TEAA/10% CH₃CN, B: 10% TEAA/90% CH₃CN The absorption of the ferrocene can be neglected in the case of this minor amount. For calculating the yield, the absorption values are considered for the corresponding dNMPs.

Triethylammonium-(5-Ferrocenylpentyl)-(2'-Deoxythymidine-5')-Phosphate
MS (ESI): ($C_{25}H_{33}FeN_2O_3P$, 576.16): m/z=(575.1 [M-H]); (449.0 [M-thymine-H]⁻); (383.0 [M-thymine-Cp-H]); (351.1 [Fc—(CH₂)₅—O—PO3]); (285.1 (CpFe—(CH₂)₅—O—PO₃]); (125.2 [thymine-H])

Triethylammonium-(5-Ferrocenylpentyl)-(2'-Deoxycytidine-5')-Phosphate
MS (ESI): ($C_{24}H_{32}FeN_3O_7P$, 561.13): m/z=(560.1 [M-H]);

Triethylammonium-(5-Ferrocenylpentyl)-(2'-Deoxyguanosine-5')-Phosphate

MS (ESI): ($C_{25}H_{32}FeN_5O_7P$, 601.14): m/z=(600.1 [M-H]);
Triethylammonium-(5-Ferrocenylpentyl)-(2'-Deoxyadenosine-5')-Phosphate
MS (ESI): ($C_{25}H_{32}FeN_5O_6P$, 585.14): m/z=(584.1 [M-H]$^-$); (448.8 [M-adenine-H]$^-$); (383.1 [M-adenine-Cp-H]$^-$); (350.9 [Fc—($CH_2)_5$—O—$PO_3$]$^-$); (285.1 [CpFe—($CH_2)_5$—O—$PO_3$]$^-$); (134.2 [adenine-H]$^-$) (586.0 [M+H]$^+$) (352.1 [Fc—($CH_2)_5$—O—$PO_3$+H]$^+$); (136.2 [adenine+H])

Ferrocenyl-Linked 4-mer

The sequence $^{5'}$TGAC$^{3'}$ was prepared with the automated oligonucleotide synthesis (1 μmole). The dimethoxytrityl group at the terminal of the last nucleotide was then cleaved manually and further processed in a way as were the monomers. The preparative HPLC was carried out under modified conditions.

HPLC: $RP_{18}$ column, flow 4 ml/min. 10%–50% B in 40 min. and 10 min. at 50%; A: 90% TEAA/10% $CH_3CN$, B: 10% TEAA/90% $CH_3CN$ Retention time 4-mer: 43 min.

MS (ESI): ($C_{54}H_{69}FeN_{15}O_{25}P_{49}$ 1507.28): m/z=(1506.9 [M-H]); (1064.5 [M-cytidine-CpFe—OH]); (619.0 [pApC])

Ferrocenyl-Linked 27-mer

The 27-mer having the sequence
$^{5'}$TTC CTC CTT CCT TCC TTC CTT CCT CCC$^{3'}$
was prepared on the oligonucleotide synthesizer and the ferrocene was manually added analogously with the monomers and the 4-mer.

Analysis by means of HPLC was carried out under the same conditions as in the case of the 4-mer: Retention time of ferrocenyl-linked 27-mer: 35.3 min.

What is claimed:

1. A process for preparing a metallocene-phosphoramidite conjugate, comprising:
   a) reacting a metallocene with a dicarboxylic acid anhydride or chloride to generate a metallocenoylalkyl carboxylic acid (I);
   b) reducing the compound obtained in step a) to generate an alcohol; and
   c) reacting the alcohol obtained in step b) with a phosphoramidite derivative to generate said metallocene-phosphoramidite conjugate.

2. The process of claim 1, wherein the metallocene is a transitional metal metallocene selected from the group consisting of ferrocene, ruthenium and osmium.

3. The process of claim 1 or 2, wherein the phosphoramidite derivative used in step c) is chloro-N,N-diisopropylamino-cyanoethoxyphosphite.

4. A method for electron-microscopically detectable labeling of an isolated nucleic acid, comprising labeling said nucleic acid with a metallocene-phosphoramidite conjugate, wherein said metallocene-phosphoramidite conjugate comprises one or a plurality of metallocene units and one or a plurality of phosphoramidite units.

5. The method of claim 4, wherein said labeling takes place during synthesis of said nucleic acid.

6. A method for cutting DNA, comprising exposing said DNA to metallocene-labeled oligonucleotides.

7. The method of claim 4, wherein the metallocene-phosphoramidite conjugate comprises at least one metallocene linked to at least one phosphoramidite via a spacer.

8. The method of claim 4, wherein the metallocene-phosphoramidite conjugate comprises a plurality of metallocenes.

9. The method of claim 8, wherein one or a plurality of the metallocenes is a transitional metal metallocene.

10. The method of claim 8, wherein one or a plurality of the metallocenes is selected from the group consisting of ferrocene, ruthenocene and osmocene.

11. The method of claim 7, wherein the spacer is a $C_1$–$C_{10}$ alkyl group.

12. The method of claim 8, wherein the metallocenes are identical.

13. The method of claim 4, wherein one or a plurality of the phosphoramidite units originates from the compound chloro-N,N-diisopropylamino-cyanoethoxyphosphite.

14. The method of claim 13, wherein the metallocene-phosphoramidite conjugate is metallocenylalkyl-(2-cyanoethyl)-diisopropylamidophosphite, the metal being a transitional metal selected from the group consisting of iron, ruthenium and osmium.

* * * * *